United States Patent [19]

Toter

[11] Patent Number: 4,642,105
[45] Date of Patent: Feb. 10, 1987

[54] GASTRIC DRAINAGE SYSTEM

[76] Inventor: Kimberly A. M. Toter, 830 Tanner Dr., Wayne, Pa. 19087

[21] Appl. No.: 757,607

[22] Filed: Jul. 22, 1985

Related U.S. Application Data

[63] Continuation-in-part of Ser. No. 581,665, Feb. 21, 1984, abandoned.

[51] Int. Cl.$^4$ .............................................. A61M 1/00
[52] U.S. Cl. .................................. 604/323; 604/335; 604/350
[58] Field of Search ............... 604/317, 318, 323, 335, 604/350, 324; 137/119, 512.3, 533, 533.17; 128/760, 766, 767, DIG. 24

[56] References Cited

U.S. PATENT DOCUMENTS

| | | | |
|---|---|---|---|
| 3,231,901 | 2/1966 | Kennedy | 128/DIG. 24 |
| 3,270,790 | 9/1966 | Clark | 128/DIG. 24 |
| 3,529,599 | 9/1970 | Folkman et al. | 604/323 |
| 3,683,894 | 8/1972 | Villari | 128/767 |
| 3,858,750 | 1/1975 | Grall | 220/208 |
| 3,906,935 | 9/1975 | Raia et al. | 128/DIG. 24 |
| 4,384,580 | 5/1983 | Leviton | 604/323 |

Primary Examiner—C. Fred Rosenbaum
Assistant Examiner—J. C. Kruter

[57] ABSTRACT

A novel self actuating anti-reflex device is provided having two anti-reflex valves in fluid connection with each other and cooperatively functioning whereby the first self actuating valve permits passage of fluid and/or gaseous matter therethrough yet senses fluid or gaseous pressure within, for example, an attached receptacle for receiving the matter being passed therein and effectively closes the passageway to the receptacle in response to the fluid and/or gaseous pressure, whereby the second anti-reflex device self actuates permitting fluid and/or gaseous matter to exit therefrom wherein the second anti-reflex valve may optionally be made inoperative. A novel, fully portable drainage collection system incorporating the foregoing self actuating anti-reflex device is also provided and made adaptable for use in connection with the drainage of gastric matter using conventional gastric systems including suction systems in conjunction with the gravity drainage of gastric matter from patients.

9 Claims, 17 Drawing Figures

GASTRIC DRAINAGE SYSTEM

This application is a continuation-in-part application of prior co-pending application Ser. No. 581,665, Filed Feb. 21, 1984, now abandoned.

BACKGROUND OF THE INVENTION

This invention relates generally to medical apparatus for the drainage of gastric fluids, to an improved anti-reflux valving system, and more specifically to a universal gastric drainage system which is adaptable to standard gastric tubes including orogastric, nasogastric, and the like.

The present invention relates to a portable, disposable gravity drainage system which can be used alone or in conjunction with various standard suction systems.

Heretofore, generally stationary suction systems have been used to supply continuous and/or intermittent suction for purposes of evacuating gastric contents at various times and for various purposes as are known in the art. These systems are bulky and thus cannot realistically accommodate the patient and/or medical needs requiring gastric drainage during transport and/or movement of the patient. Moreover, various medical conditions may require or dictate that gravity drainage be utilized.

Typically, gravity drainage collection devices employ belts, straps, eyelits and the like to achieve portability. Problems associated with such portable systems are, inflexibility insofar as providing an acceptable method of support for hanging systems, and lack of rigidity in the support devices used. Straps and belts rely on torous, rectangular or cylindrical objects for support. Attachment to flexible items such as clothing or draping is only possible with the use of tape or clips. In addition, straps do not add to the stability of the drainage system with respect to rigidity in maintaining the system in operable conditions; e.g., unfolded, open or straight. Shifting of weight in the system can go relatively unopposed or folding can occur making patient ambulation difficult.

While there are various medical drainage collection devices known in the prior art these all have various disadvantages and do not address problems specific to and are thus not readily adaptable to conditions specific to gastric drainage requirements and/or to requirements of standard gastric tubes and suction devices. Moreover, it is believed that the anti-reflux valving mechanism of the present invention addresses the foregoing specific conditions and/or requirements and solves problems with respect to a portable gravity drainage system heretofore unresolved by the prior art.

U.S. Pat. No. 4,334,537, to Peterson discloses an improved anti-reflux valve, however, there is no provision for release of pressure build up or gastric gases upon closure of the reflux mechanism and it is therefore not responsive to gastric conditions including those prevelent in the gravity drainage of gastric fluids and/or gases either alone or in combination with a fluid receptacle.

U.S. Pat. No. 3,661,143 is directed to a system for the drainage and collection of body fluids and arranges various chambers to provide a hydrostatic pressure differential together with a disclosed gas gap, however, it does not provide versatility and adapatability to gastric systems and does not provide an anti-reflux valving mechanism to prevent gas and/or fluid matter traveling back to the patient, nor is there any provision for exiting of gaseous matter upon closure of the drainage tube from the patient to the collection receptacle.

U.S. Pat. No. 3,722,502 shows a multiple liquid sample collection apparatus joining a plurality of separable collection units however, there is no provision for anti-refluxing means either when considered as a unit or as between separable units and thus would not satisfactorily function in the environment of the drainage collection system of the present invention.

U.S. Pat. No. 3,529,599 to Folkman teaches a rigid handle which provides support to the flexible drainage system, however, the handle provides no means for support to any object other than those which utilize belts or straps or protrusions of geometric configurations capable of vertically hanging the bag; they do not provide means for preventing the accidental disengagement from such devices.

U.S. Pat. No. 3,683,899 to Viltari and U.S. Pat. No. Re. 30,607 to Manschot et. al teach a support rod with strips which is deficient in that additional hanging support is required even though the rod does provide stabilization cords.

U.S. Pat. No. 3,722,502 to Resuner et al. discloses a handle, however, it provides no rigidity to the system and additional support is required. Moreover, folding of the bag will directly effect volume, thus any calibrations will be inaccurate. Also, a side to side shifting of the bag in transport (such as a patient walking) could be accentuated by liquid and cause a major shift in the collection portions position, thus further limiting the functionality of the device.

Exemplary of other drainage devices are, for example, U.S. Pat. Nos. 4,393,880, 4,338,480 and Re. 30,607 relating to urine receptacles, and U.S. Pat. Nos. 4,278,089 and 4,015,605 relating to wound drainage receptacles and receptacles containing sampling conduits and the like.

In view of the various problems, disadvantages and the lack of flexibility of various known collecton receptacles as these relate to the conditions of gastric drainage and the standard gastric tubes used in conjunction therewith, the present invention solves heretofore unresolved problems and fills a long felt need for a device adaptable to such conditions. In fact the various products currently used for gastric drainage conditions, were designed for other intended purposes, and used only in the absence of specific systems which properly accommodate the conditions present during drainage of gastric fluids. Not only do such products, including the prior art drainage devices have various drawbacks and limitations with respect to use in conjunction with gastric fluids and/or gases but many such devices and practices violate the safety of the patient as well.

For example, an asepto syringe has been used to irrigate gastric tubes however such syringes naturally have an airlock and will not function to promote gravity drainage. Moreover they are not readily adapted for use with gastric tubes, there is no anti-reflex valve to prevent fluids from being transported back into the patient, they do not provide a means to accurately monitor the drainage therethrough, and the amount of fluids coming from the patient can only be read when the syringe is inverted which would thus place the syringe in a position to discharge contents back into the tubing leading to the patient. The asepto syringe has additional disadvantages with respect to sanitary disposal, and the like.

Other bags and/or receptacles used for gravity drainage generally have no anti-reflex valve or are not adaptable to conditions specific to gastric drainage, contain no means to calibrate the asperate, are not transparent and therefore cannot be effectively used to monitor the gastric fluids, are not adaptable to standard gastric devices, cannot be readily secured thereto and thus do not permit a sanitary method of collection and disposal of the gastric matter either when the patient is statioery or when in transit. In many instances the gastric tube is clamped and/or plugged when the patient is in transit which generally causes risk to the patient such as, for example, gastric and/or abdominal distention as well as other gastric or gastrointestinal disorders. Also, these products do not provide a sterile environment from which the contents may be extracted for testing purposes and the like.

SUMMARY OF THE INVENTION

Accordingly, it is an object of the present invention to remedy the foregoing defects and disadvantages existing in the prior art drainage and collection systems.

A further object of the present invention is to provide a portable gastric drainage system for the proper collection and monitoring of character and amount of gastric matter.

It is another object of the present invention to provide a transparent calibrated drainage receptacle containing in combination therewith a novel anti-reflux valving mechanism for use in the drainage of gastric matter.

Yet another object of the present invention is to provide a portable gastric drainage system which is readily adaptable to standard gastric tubes and systems, including being readily adaptable to and used in conjunction with suction systems.

It is yet a further object of the present invention to provide an anti-reflux valving system which prevents the discharge of gastric matter including fluids and/or gases back into the gastric tubes leading to the patient while at the same time providing means for relief of gastric matter and/or pressure through an automatically actuating relief valve.

Still yet a further object of the gastric drainage system of the present invention having the above novel anti-reflux relief valve is to provide first means for permitting gastric matter to enter the drainage receptable and a second self actuating means wherein upon closure of the first self actuating means in response to gastric matter including either fluids or gaseous matter, the second self actuating means permits the release of gaseous matter and/or fluid matter in a manner which prevents gasatric matter from backing up into the gastric tubes leading to the patient.

Still yet a further object of the present invention is to provide in combination with first and second anti-refluxing mechanisms a third pressure relief means within the drainage receptacle whereupon pressure is relieved from the receptacle to prevent premature closure of the first means but in such an instance, to vent the receptacle to permit pressure relief and thus the opening of the first means to permit and/or encourage the unattended free flow of gastric matter into the drainage receptacle.

It is yet another object of the present invention to provide the foregoing gastric drainage system which can be connected serially or otherwise to a plurality of gastric systems of the present invention, by, for example, interconnecting the systems by providing, for example, fluid connection between the second anti-reflux means and the entry port of a second gastric drainage system.

It is still yet a further object of the present invention to provide the gastric drainage system of the present invention with fastening means capable of attaching to the patient and/or other stationary and/or movable fixtures to permit the continuous gravity drainage of gastric matter under various conditions including patient relocation and/or transport.

It is another object to improve the flexibility of portable systems by providing stiffness and rigidity accomplished through the intimate joining of e.g., an unplasticized vinyl to the plasticized collection portion of the gravity drainage system. Moreover, this joining can be accomplished to the plasticized vinyls (which are more common to the collection portions of gravity drainage systems) through heat sealing.

Still yet a further object of the present invention is to provide for collection of gastric matter in a sterile medium in a receptacle containing a further valve means permitting the removal of the gastric matter for testing or otherwise, as well as providing other valving systems which contain the gastric matter within the closure for the sanitary disposal of same.

The above and other objects and advantages of the invention will be better understood by reference to the following detailed description of the preferred embodiment when considered in connection with the accompanying drawings and appended claims.

DETAILED DESCRIPTION OF THE PREFERRED EMBODIMENT

Figure 1:
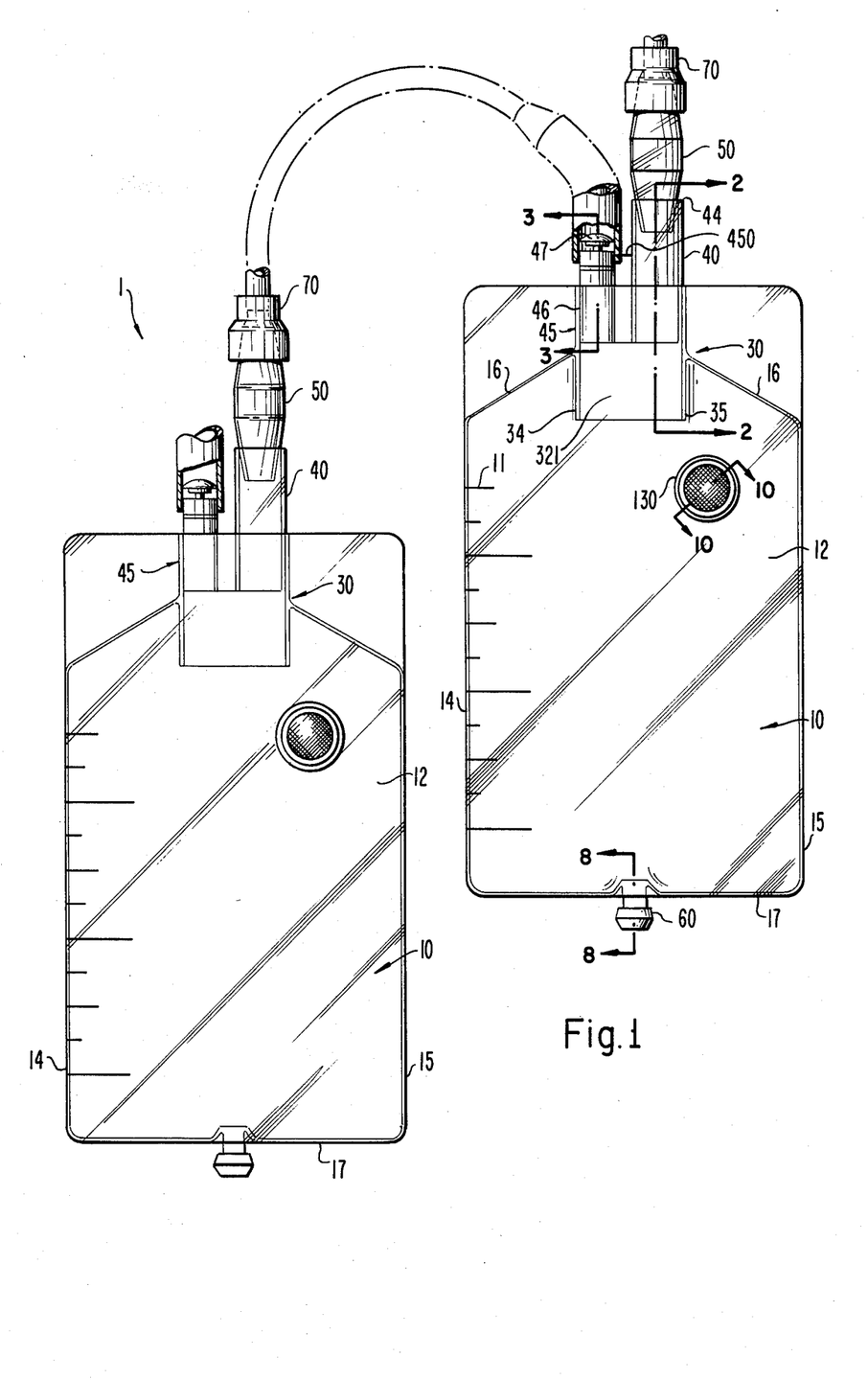
FIG. 1 is a partial, elevational view of the preferred embodiment of the gastric drainage system in accordance with the present invention.

Referring now to the drawing figures, and particularly FIG. 1, the preferred embodiment of the gastric drainage device of the present invention is shown and designated generally by numeral 1.

Gastric drainage device 1 generally compriese a transparent plastic expandable receptacle 10 which is preferably made of a heat-sealable-type plastic, such as polyethylene film, which is preferably about 5 mil in thickness and is folded over on itself and heat sealed to form such a receptacle. Receptacle 10 further includes anti-reflux valve system 30 and preferably a push pull valve 60. Preferably gastric drainage system 1 further includes adaptor means 50 and breather valve means 130.

Transparent receptacle 10 is preferably integral with anti-reflux valve means 30. Adaptor means 50 is connected with gastric tube means 70 which is connected to tubing to the patient permitting the gravity flow of gastric matter there through into adaptor means 50 through anti-reflux means 30 and into receptacle 10 where the gastric matter is collected. Gastric drainage system 1 is in the preferred embodiment transparent so that one can visually monitor the flow of the gastric matter throughout the gastric drainage system and into receptacle 10. Receptacle 10 further has calibration markings 11 so that the volume of gastric matter can be monitored.

With reference to FIG. 1, receptacle 10 is fabricated by taking a sheet of heat sealable plastic material and folding it upon himself as shown. The containment bag or receptacle 10 is fabricated by heat sealing front wall 12 to back wall 13 along edges 14, 15, 16 and 17, As is best seen from FIGS. 1 and 2 front wall 12 of containment bag 10 diverges from the rectangular back 13 forming edges 16 which are in the preferred embodiment formed by cutting and folding front wall 12 to form anti-reflux valve 30 with the flaps of edges 16 being folded in back of front wall 12 and being heat sealed to rear wall 13 thus providing stiffness which will function to keep the containment walls 12 and 13, respectively, in slightly spread condition. As thus fabricated, receptacle 10 forms a flexible expansible receptacle which is capable of withstanding acidic gastric matter which may be in the form of fluids, particulate matter, gaseous matter, and the like. As thus constructed, receptacle 10 expands in the presence of the gastric matter wherein the volumetric expansion of receptacle 10 creates a negative pressure within receptacle 10 and thus encourages the gravity drainage of the gastric material from the patient into the collection receptacle.

Referring now to FIGS. 1 through 4, anti-reflux valve 30 of the presnet invention is in the preferred embodiment an integral unit comprising spout means 40, first anti-refluxing means designated generally as 32 for permitting gastric matter to pass therethrough into collection receptacle 10, yet upon sensing of fluid and/or gaseous pressures from within receptacle 10 flaps 321 and 322 fold upon themselves automatically closing off access between spout 40 and receptacle 10 thus preventing any gastric matter from passing from receptacle 10 through the first means 32 and back into or through anti-reflux means 30 and into, for example, passageway 33 and spout 40. Spout 40 however is in fluid communication with a second refluxing means designated generally as 45 via passageway 33 which freely communicates with spout 40 and keeps same in fluid communication with second anti-refluxing means 45 even when, for example, first anti-refluxing flaps 321 and 322 have folded upon themselves, closing first anti-refluxing means 32. As depicted, second anti-refluxing means 45 comprise a generally tubular spout 46 having a partially self actuating closure mechanism 47.

Spout 40 is preferably a tubular structure which may be produced by injection molding or other suitable processes, fabricated of a transparent plastic material such as polyethylene and the like which material is resistant to the acidic gastric matter. The materials should preferably be transparent and be of material which gives spout 40 sufficient strength to accept adaptor 50, which is made of a more rigid material, yet holds adaptor means 50 in fitted condition permitting adaptor 50 to be inserted into spout 40 in fluid tight condition while permitting removal of adaptor 50 without permanent deformation of spout 40. Spout 40 is preferably more flexible than is adaptor 50 and permits expansion of spout 40 at its entrance 44 during connection with adaptor means 50.

First anti-reflux means 32 comprises a front wall 321 and a rear wall 322 creating a fluid connection between passageway 33 and receptacle 10. front and rear walls 321 and 322 respectively are fabricated of a transparent flexible thin film material such as polyethylene and the like which may be heat sealed to the front and rear walls of receptacle 10 at juncture 31. The front and rear walls 321 and 322 respectively are themselves sealed to one another along edges 34 and 35, see FIGS. 1 and 2. First anti-eflux means 32 may be fabricated from the receptacle 10 material itself from a finger of material fabricated from front 12 and back 13 of receptacle 10 which are folded inwardly to create front wall 321 and rear wall 322 of first anti-reflux means 32 whereupon vertical edges 34 and 35 are heat sealed to their corresponding opposite wall flaps extending inside the receptacle 10.

Figure 2:
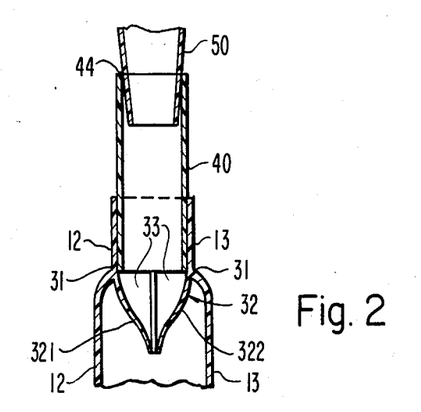
FIG. 2 is a section taken along the line 2—2 in FIG. 1 illustrating a first reflux valve means of the anti-reflex valve mechanism of the present invention.

As is best seen in FIG. 2 the front wall 12 and back wall 13 are heat sealed to spout 40 and second anti-reflux means 45, with spout 40 and second anti-reflux means 45 being further secured to each other and to receptacle 10 by a tab 450 comprising front and rear wall materials 12 and 13 respectively which are further heat sealed one to the other.

Figure 3:
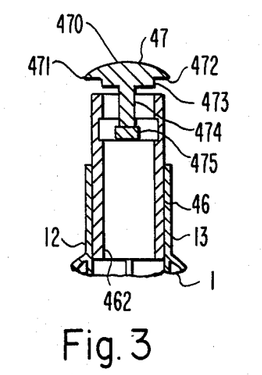
FIG. 3 is a sectional view taken along the lines 3—3 in FIG. 1 showing the second anti-reflux means of the anti-reflux valve mechanism of the present invention in the open position.
Figure 4:
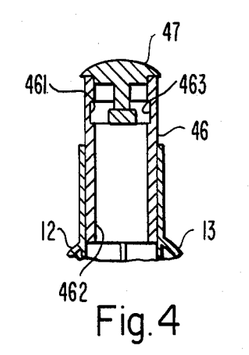
FIG. 4 is the second anti-reflux means as shown in FIG. 3 as shown in the closed position.

Referring now to FIGS. 3 and 4 the second anti-reflux means 45 having closure means 47 is best shown, with closure means 47 further comprising a cap 470 having protruding edges 471 which in the closed position (FIG. 4) protrudes out beyond the outer diameter of spout 46. Inner shoulder 473 snugly fits within the inner diameter of spout 46 and is integral with stem 474 having a diameter smaller than the inner diameter of spout 46. Stem 474 is also integral with T section 475. Spout 46 has an internal section 461 having a diameter greater than the internal section designated 462 creating a shoulder 463 and a passageway through which T section 475 freely slides. In the open most position of the second anti-reflux means 45, T section 475 abuts against shoulder 463.

In operation, second anti-reflux means 45 is self-actuating in that it permits the passage of gastric matter therethrough and particularly gaseous matter to be released therethrough when first anti-reflux means 32 is closed. The passage of the gastric matter through spout 40 and passageway 33 up through spout 46 effectively raises shoulder 473 of mechanism 47 (FIG. 3) permitting the gastric matter to exit to atmosphere. Construction of second anti-reflux means 45, however, permits the self actuating device to be made inoperative by forcing shoulder 473 within the interior of spout 46 which effectively places cap 470 in fitting and fluid tight connection with spout 46 in a manner which would be unresponsive to the pressure of the gastric matter thereon and would thus effectively close spout 46 to atmosphere. While it is conceivable that for certain operations second anti-reflux valve 45 would desirably be placed in inoperative condition, in the preferred embodiment it is kept in self-actuating condition.

Figure 8:
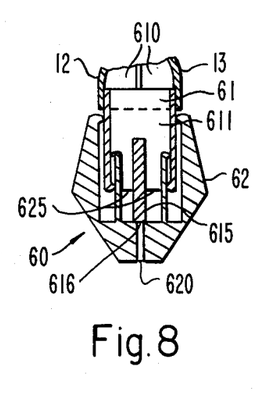
FIG. 8 is a sectional view taken along the lines 8—8 in FIG. 1, showing the valve of the gastric drainage system of the present invention in closed position.
Figure 9:
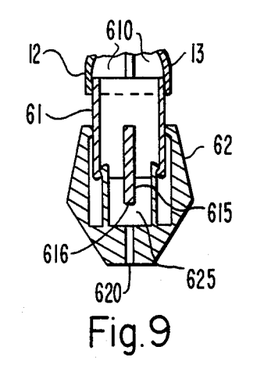
FIG. 9 is the valve of FIG. 8 shown in the open position.

With reference now to FIGS. 1, 8 and 9, push pull valve means 60 is located in the base of receptacle 10 and comprise two mating sections, generally referenced as plug 61 and seat 62. As is best seen in FIG. 8, valve means 60 is secured to receptacle 10 by virtue of plug 61 being heat sealed thereto wherein plug 61 is in fluid communication with the inside of receptacle 10. As is best seen from comparing FIGS. 8 and 9 when valve 60 is in the open position (FIG. 9) the gastric matter flows through passageway 61 into passageway 61 and into passageway 625. T-shaped stem 615 has a diameter less than that of passageway 625 but greater than exit passageway 620. With reference to FIG. 8, which shows valve 60 in the closed position, base 616 of stem 615 abuts seat base 620, sealing exit port 620 and preventing any gastric matter from exiting receptacle 10 through valve 60.

Figure 10:
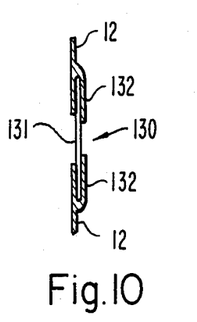
FIG. 10 is a sectional view taken along the lines 10—10 in FIG. 1 of a venting mechanism for the gastric drainage system of the present invention.

With reference now to FIGS. 1 and 10 a preferred embodiment of the present invention further includes breather valve means 130 which is preferably incorporated within receptacle 10 in a position relatively close with that of anti-reflux means 30, which is usually above typical fill levels of receptacle 10. As is best seen in FIG. 10, breather valve 130 comprises a gas permeable woven fibrous material which will permit gas to escape from the interior of receptacle 10 to atmosphere and not visa versa, yet will preclude any loss of fluid or any gastric matter therethrough. Gas permeable material 131, as is known in the art, is heat sealed within the front flap 12 of receptacle 10 using flanges 132 fabricated of the same heat sealable material as is receptacle 10, see FIG. 10.

Figure 5:
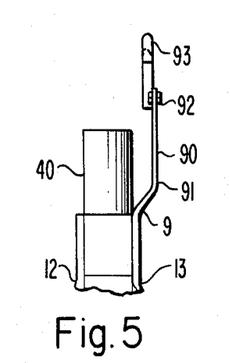
FIG. 5 is a partial side elevation of the fastening means of the gastric drainage system of the present invention of FIG. 1.

Still yet a further feature of the present invention is shown in FIG. 5 wherein fastener means 9 is shown as being heat sealed to rear wall 13 of receptacle 10 behind receptacle 10 as viewed from FIG. 1, preferably in a position in close proximity with spout 40. Fastener means 9 is fabricated of a strong but flexible material which is heat sealable to receptacle 10 and can support the entire weight of receptacle 10 when filled with gastric matter. Fastener means 9 further includes a strip of flexible mateiral 91 which is secured to alligator clip 93 with fastener 92 which is preferably a rivet. Aligator clip 93 can be utilized to fasten gastric drainage system 1 either to the patient or other convenient locations which would permit proper drainage of the gastric matter from the patient yet permit mobility and portability of gastric drainage system 1 and at the same time insure that receptacle 10 is maintained in substantially upright condition.

Figure 11A:
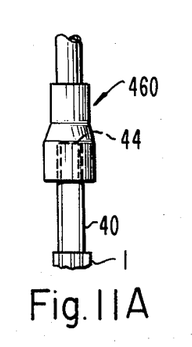
FIG. 11A is an embodiment of the gastric drainage system of the present invention as connected to a standard plastic nasogastric tube.
Figure 11B:
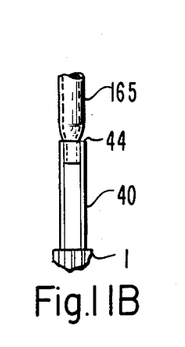
FIG. 11B is an embodiment showing the gastric drainage system of the present invention as connected to a standard rubber nasogastric tube.

As is best seen in FIGS. 11A and B, gastric drainage system 1 as thus far described, is fully adaptable to standard plastic gastric tubes such as the nasogastric tube 460 (FIG. 11A) and the standard rubber nasogastric tube 165 (FIG. 11B).

Figure 6:
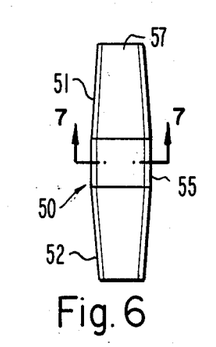
FIG. 6 is a side elevational view of the adaptor coupling member of the gastric drainage system of the present invention.
Figure 7:
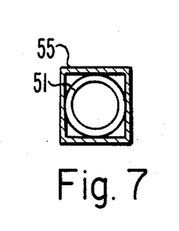
FIG. 7 is a plan view of the coupler adaptor as shown in FIG. 6.

In yet another embodiment of the present invention a frusto-conical adaptor means 50 is provided as is shown in FIGS. 6 and 7 having frusto-conical sections 51 and 52 connected by gripping section 55 which is preferably square in cross-section as is shown in FIG. 7. Adaptor means 50 is preferably comprised of a transparent thermoplastic or thermoset material providing a fluid passageway 57 therethrough, passageway 57 being of a suitable diameter to pass various gastric matter therethrough and being fabricated of an acid resistant resilient durable plastic material which can be fabricated from a suitable plastic such as polyethylene and the like by means of injection molding or other suitable processes. Adaptor means 50 must be sufficiently resilient ot enable insertion into and in fluid tight communication with spout 40 utilizing finger pressure. Mid-section 55 is adapted for grasping by fingers such as the thumb and index fingers for insertion and removal of adaptor means 50 from spout 40 as well as to promote ease of fluid connection with various types of gastric tubes, suction devices, and the like.

Figure 12A:
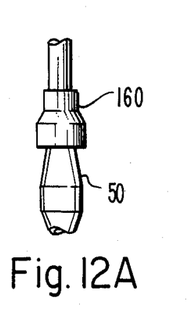
FIG. 12A is a second embodiment of the gastric drainage system of the present invention showing an alternate connection to a standard plastic nasogastric tube.
Figure 12B:
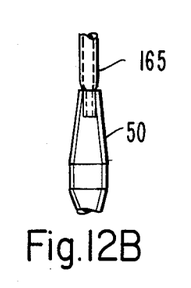
FIG. 12B is yet another embodiment of the gastric drainage system of the present invention showing an alternative method of connection to a standard rubber nasogastric tube.
Figure 13:
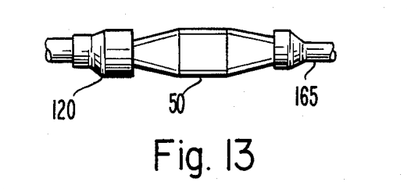
FIG. 13 is another embodiment showing the adaptor connector of the present invention in an alternative connection with a standard levin tube and to suction.

As is seen from FIGS. 12A and 12B, gastric drainage system 1 is utilized in conjunction with adaptor means 50 to secure same with a standard plastic nasogastric tube 160 and a standard rubber nasogastric tube 165. By using adaptor means 50 together with gastric drainage system 1, the gastric drainage system of the present invention may be made fully interchangeable with and be utilized in combination with various gastric tubes. Moreover, adaptor 50 is readily adaptable with standard suction systems and thus standard gastric tubes connected to adaptor 50 can be readily connected to a suction system and changed to gastric drainage system 1 and visa versa. FIG. 13 shows adaptor means 50 utilized in combination with suction system 120 to interconnect with rubber tube 165 which in this instance is spread to accommodate frusto-conical section 51 in female interconnection therewith in contradistinction to male interconnection as shown in FIG. 13.

In operation of gastric drainage device 1 as thus far described, gastric drainage device is in fluid connection wih a standard gastric tube which is in communication with the patient. Gastric matter drains through the standard gastric tubes through spout 40 and anti-reflex valve 30 and into receptacle 10 causing expansion thereof and a negative pressure differential to thus encourage the gastric flow of matter from the patient to gastric drainage system 1 for collection in receptacle 10. Under conditions wherein excess pressure. either gaseous or fluid develops within receptacle 10, first antireflux means 32 automatically actuates closing the passageway from spout 40 through and into receptacle 10. In the instance further gastric matter and particularly gaseous matter is expelled through the standard gastric tube into the gastric drainage system 1 a build-up of such matter accumulates in passageway 33 and could ultimately back up through spout 40 and prevent free flow of gastric matter from the patient to the collection receptacle. The present invention however provides a second anti-reflux means 45, which is a self actuating means permitting the flow of gastric matter from the patient and through second anti-reflux means 45 permitting same to exit through spout 46 to atmosphere. While it is contemplated that the second anti-reflux means 45 will be activated only such periods of time to permit gaseous flow therethrough into atmosphere, in another embodiment of the present invention the second anti-reflux means 45 can be placed in fluid connection with a second gastric drainage system (not shown) permitting the evacuation of gaseous matter including fluids therethrough and thus it is contemplated that a series of such gastric drainage systems may be arranged to collect gastric matter for over a period of time without adversely affecting patient's health or safety.

In the preferred mode of operation, breather valve means 130 is provided in the instance that excessive gaseous build-up occurs within receptacle 10 whereby under these conditions the gaseous material can exit or vent to atmosphere without the attendant loss of gastric fluids therethrough to relieve gaseous pressure, and thus in this instance, gaseous pressure within receptacle 10 would not reach threshold levels to trigger closure of the first anti-reflux means 32. In the instance such closure is triggered and second anti-reflex means 45 is actuated, it is anticipated that gastric pressure within the receptacle 10 would be relieved by virtue of breather valve means 130. This would permit first anti-reflux means 32 to reopen and permit uninterrupted gravity drainage and/or flow of gastric material without attendant pressure build-up and back up of the gastric material from gastric drainage system back through the standard gastric tubes and into the patient since passageway 33 accords a second receptacle for collection of gastric matter until conditions within receptacle 10 permit the preferred flow of the gastric matter directly into receptacle 10.

Gastric drainage system 1 of the present invention permits the easy removal and/or disposal of the gastric matter in that second anti-reflux means 45 can be inactivated by inactivating self actuating closure member 47 by finger pressure asserted on member 470 placing shoulder 473 in fitted in fluid tight communication with spout 46. First anti-reflux valve 32 automatically activates to close the passageway from within receptacle 10 out through spout 40 upon any gaseous and/or fluid pressure bearing upon relfex valve wall 321 and 322 causing same to fall one upon the other closing off the passageway and thus preventing any fluid escape therethrough. It is further contemplated that valve 60 can be opened should samples of the gastric matter or other matter contained within receptacle 10 be desired to be either entirely removed from receptacle 10 or portions of such matter be removed for purposes of testing, analysis, and the like.

Figure 14:
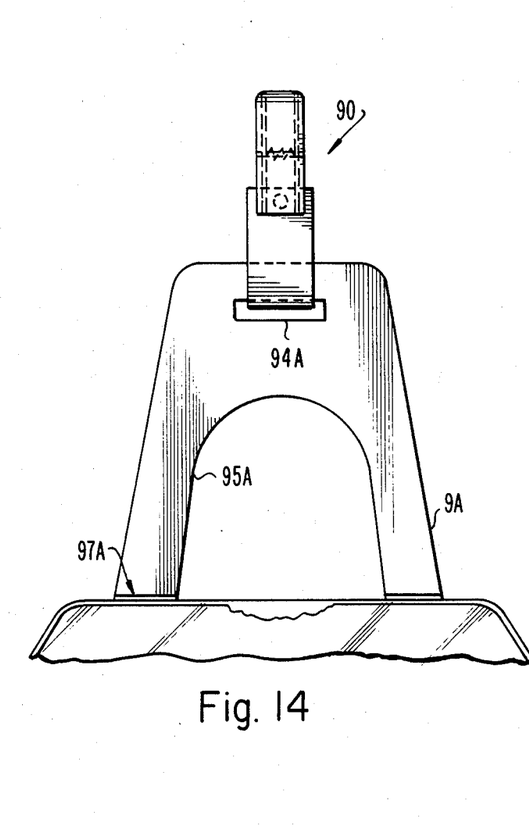
FIG. 14 is an elevational view showing the preferred support system of the present invention.
Figure 15:
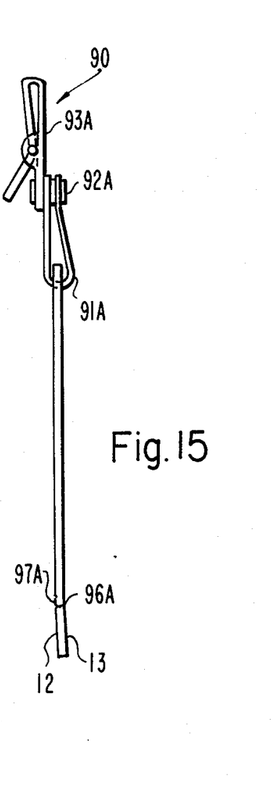
FIG. 15 is a side elevation of the support system as in FIG. 14.

Referring now to FIGS. 14 and 15, the preferred embodiment of the support system is designated by numeral 90. The support system is compromised of an unplasticized vinyl strip 9A, which is 13–16 mils in thickness and is heat sealed at the base 96A to the top of the collection portion of the drainage system sides 12 and 13. the support is rigid in property and provides stiffness and resilience to folding through elastic modulus. The support provides a means for drainage tube access to the spout of entrance of the collection portion by means of an archway 95A, which is comprised of a smooth and generous radius to eliminate stress concentrations which could lead to folding of collections receptacle 10 under compressional loading. The support contains an accessway 94A for passage of a mylar strip 91A, which is riveted by snap type connected 92A for means of connecting solid spring loaded metal clip 93A and to allow for connection of same to support strip 9A. The strip is additionally creased at the base at location 97A, to facilitate folding of rigid support system 90 about gravity drainage collection portion 10 for convenience in packaging and simplicity of storage. The drainage collection system as thus far described comprises support means foldably connected with an expandable receptacle 10 for attaching the drainage collection system 1 to a patient and maintaining the expandable receptacle 10 in unfolded condition without interference with the expandability of expandable receptacle 10 and without interference with the operation of the first anti-reflux means 32.

While it is contemplated that the gastric drainage system of the present invention will be most suitably used in connection with gastric drainage conditions, the features of the present invention as thus far shown and described may be suitable for other conditions as is known to one skilled in the art by a full reading of the specification, drawings and appended claims.

What is claimed is:

1. A medical drainage valve system for the collection of gastric fluids comprising:

first anti-reflux means having wall means for receiving incoming matter including fluid and gaseous matter, for permitting said matter to pass therethrough whereafter said matter becomes outgoing matter, and flexible wall means for automatic collapsing and closing said first anti-reflux means in response to gas or fluid pressure resulting from said outgoing matter to prevent said matter from passing in or out of said first anti-reflux means; and second anti-reflux means including a passageway in fluid communication with said first anti-reflux means, said second anti-reflux means having an inlet between the confines defined by said wall means of said first anti-reflux means and including within the first anti-reflux means for direct fluid communication with the atmosphere self-actuating valve means in fluid communication with said passageway for sensing fluid or gaseous pressure and in response thereto permitting said outgoing matter to pass there-through.

2. A drainage collection system including said antirelux device of claim 1, further comprising a expandable collection receptacle in fluid communication with said first antireflux means to collect said matter which passes therethrough, said collection receptacle being expandable in response to receipt of said matter, whereby a negative pressure differential within said receptacle is created promoting flow of said matter into said receptacle.

3. A drainage collection system as in claim 2, further comprising breather means integral with said receptacle for permitting passage of gaseous matter but not fluid matter from within said receptacle whereby upon premature closure of said first anti-reflux means due to gaseous pressure within said receptacle in instances of excessive development of gaseous pressure, the closure of said first anti-reflux means is effectuated and said breather means provides for venting of said gaseous mater until said pressure within said receptacle is relieved permitting said first anti-reflux means to pass said matter therethrough.

4. A drainage collection system as in claim 3, further comprising a plurality of units comprising said anti-reflux device in combination with said receptacle wherein said plurality of units are serially connected one to the other by fluid interconnection means in fluid connection with said second anti-reflux means of one said unit and said first anti-reflux means of the other said unit, whereby upon closure of said first anti-reflux means of said one unit, said matter flows through said passageway and second anti-reflux means of said unit, through said fluid interconnection means and into said first antireflux means of said other unit.

5. A drainage collection system as in claim 2, further comprising support means foldably connected with said expandable receptable for attaching said drainage collection system to said patient and maintaining said expandable receptacle in unfolded condition without interference with the expandibility of said expandible receptable and without interference with the operation of said first means.

6. A drainage collection system as in claim 3 for use with standard gastric tubes including naso-gastric and levin tubes, wherein said first anti-reflex means includes spout means for receiving said matter comprising a generally tubular member adapted for fitted, fluid connection with said gastric tubes.

7. A drainage collection system as in claim 6 for use in the drainage of gastric matter and for use in combination with standard suction systems further comprising adaptor means for fitted, fluid connection with said spout means and said gastric tubes for passage of gastric matter therethrough whereby said adaptor means as connected to said gastric tubes is readily and interchangeably connectable with said suction systems and said drainage collection system.

8. A drainage collection system including the medical drainage valve system as in claim 1, further comprising:
an expandable receptacle for collection of said gastric fluids said receptacle expanding in connection with the receipt of said gastric matter creating a negative pressure within said receptacle; and
support means foldably connected with said expandable receptacle for attaching said drainage collection system to said patient and maintaining said expandable receptacle in unfolded condition without interference with the expandability of said expandable receptacle and without interference with the operation of said first anti-reflux means.

9. A drainage valve system as in claim 1, further comprising third means for selectively inactivating said self-actuating valve means whereupon said self-actuating valve means is effectively closed preventing passage of said outgoing matter therethrough.

* * * * *